United States Patent
Schöller et al.

(10) Patent No.: US 8,863,106 B2
(45) Date of Patent: Oct. 14, 2014

(54) METHOD AND DEVICE FOR UPDATING MEDICAL APPARATUS

(75) Inventors: Bernd Schöller, Karlsruhe (DE); Thomas Marx, Hamburg (DE)

(73) Assignee: Weinmann Gerate fur Medizin GmbH & Co. KG, Hamburg (DE)

( * ) Notice: Subject to any disclaimer, the term of this patent is extended or adjusted under 35 U.S.C. 154(b) by 1165 days.

(21) Appl. No.: 12/148,516

(22) Filed: Apr. 18, 2008

(65) Prior Publication Data
US 2008/0271010 A1 Oct. 30, 2008

(30) Foreign Application Priority Data
Apr. 18, 2007 (DE) .......................... 10 2007 018 587

(51) Int. Cl.
| | | |
|---|---|---|
| G06F 9/44 | (2006.01) | |
| G06F 9/445 | (2006.01) | |
| A61B 5/00 | (2006.01) | |
| A61N 1/39 | (2006.01) | |

(52) U.S. Cl.
CPC ................. *A61B 5/00* (2013.01); *A61N 1/3925* (2013.01); *G06F 8/65* (2013.01); *A61N 1/39* (2013.01)
USPC ........................................................ 717/168

(58) Field of Classification Search
CPC ............... G06F 8/65; G06F 8/67; G06F 8/68; G06F 8/60
USPC ............................................................ 717/168
See application file for complete search history.

(56) References Cited

U.S. PATENT DOCUMENTS

| | | | | |
|---|---|---|---|---|
| 5,103,814 | A * | 4/1992 | Maher ...................... | 128/204.18 |
| 6,564,798 | B1 * | 5/2003 | Jalde ........................ | 128/205.24 |
| 6,612,995 | B2 * | 9/2003 | Leonhardt et al. ............ | 600/532 |
| 6,934,356 | B1 * | 8/2005 | Satheesan et al. ............. | 378/62 |
| 2005/0192847 | A1 * | 9/2005 | Satheesan et al. ................ | 705/3 |
| 2006/0144396 | A1 * | 7/2006 | DeVries et al. .......... | 128/204.21 |
| 2007/0006150 | A9 * | 1/2007 | Walmsley ...................... | 717/120 |
| 2007/0044805 | A1 * | 3/2007 | Wedler et al. ............ | 128/207.14 |
| 2008/0005733 | A1 * | 1/2008 | Ramachandran et al. .... | 717/168 |
| 2008/0091092 | A1 * | 4/2008 | Al-Ali ........................... | 600/310 |
| 2008/0133265 | A1 * | 6/2008 | Silkaitis et al. .................... | 705/2 |
| 2008/0154957 | A1 * | 6/2008 | Taylor et al. ................ | 707/104.1 |
| 2009/0135196 | A1 * | 5/2009 | Holland et al. ............... | 345/589 |
| 2009/0307677 | A1 * | 12/2009 | Long et al. ..................... | 717/168 |
| 2010/0130933 | A1 * | 5/2010 | Holland et al. ............... | 604/151 |
| 2010/0192007 | A1 * | 7/2010 | Tarra et al. ......................... | 714/6 |
| 2011/0061647 | A1 * | 3/2011 | Stahmann et al. ........ | 128/202.16 |

\* cited by examiner

*Primary Examiner* — Li B Zhen
*Assistant Examiner* — Arshia S Kia
(74) *Attorney, Agent, or Firm* — Abel Law Group, LLP

(57) ABSTRACT

The method and the device are used for updating a medical apparatus that has a memory for an operating program. The memory is at least partially designed as a variable memory and is connected with an input device for a current operating program. The memory and the input device are connected to control devices, which have testing means for evaluating at least one code. At least one function of the apparatus is released only when the code agrees with a reference value.

16 Claims, 1 Drawing Sheet

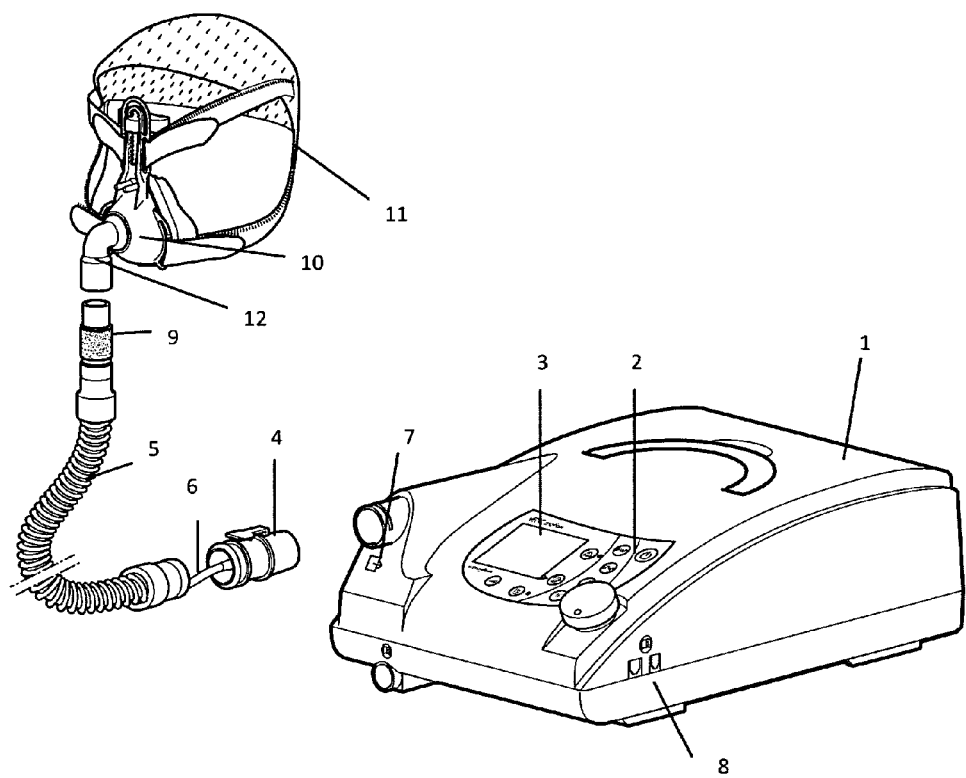

METHOD AND DEVICE FOR UPDATING MEDICAL APPARATUS

The invention concerns a method for updating medical apparatus, in which an operating program stored in the apparatus is at least partially replaced by a new operating program.

The invention also concerns a device for updating medical apparatus, said device having a memory for an operating program.

In most medical apparatus, the operating software is stored in a permanent memory and executed by a microcontroller that is designed for this software. Consequently, the software is stored in the form of unalterable program instructions, and the microcontroller cannot be upgraded and has no free capacity. In the case of software updates, memory components must be replaced, so that it becomes necessary for a specialist to disassemble the apparatus. A software update of this type is complicated and expensive, because the medical apparatus cannot be used for the duration of the update process.

In other cases, it is necessary to replace hardware in order, for example, to be able to use sensors with upgraded functionality.

Due to rapid ongoing technical developments, medical apparatus is often no longer state of the art after only a short period of use. At present, therefore, users who depend on the latest or other required functions purchase new medical apparatus on a regular basis.

It would be desirable to provide medical apparatus with an update functionality that would allow the user to upgrade his medical apparatus with the latest functions or with additional functions.

As used in the context of the present invention, a medical apparatus is understood to be an apparatus that is used for medicinal, medical, or health-related purposes, especially a measuring apparatus, diagnostic apparatus, or therapeutic apparatus, such as a ventilator, a defibrillator, an oxygen concentrator, a pulse oximeter, a pulse spectrometer, or a diagnostic apparatus for respiratory disorders.

The objective of the present invention is to design a device of the aforementioned type in such a way that the device carries out hardware and/or software updates for a medical apparatus without it being necessary to make a hardware replacement.

In accordance with the invention, this objective is achieved by virtue of the fact that the memory is at least partially designed as a variable memory and is connected with an input device for a current operating program and that the memory and the input device are connected to control devices, which have testing means for evaluating at least one code, where at least one function of the apparatus is released only when the code agrees with a reference value.

In particular, in accordance with the invention, the objective is achieved by virtue of the fact that the device of the invention for a medical apparatus consists of an internal or external input device for data input and/or data reception and of a memory device that is at least indirectly connected with said input device, with data or computing and/or counting algorithms stored in at least one memory in the memory device and with testing means that automatically compare the input or received data (here: "code") with data stored in one or more memories of the memory device, including especially after or while the code and/or the data stored in one or more memories were or are being processed (especially were or are passing through computing and/or counting algorithms), where control devices are present, which, on the basis of the comparison result determined by the testing means and only in the case of a certain well-defined code or certain well-defined codes, automatically cause the apparatus at least temporarily to be able to perform certain functions associated with these codes and cause the performance of these functions associated with the codes to be disabled by these control devices or by other means without the proper code.

A further objective of the invention is to improve a method of the aforementioned type in a way that is conducive to simple updating of the apparatus.

In accordance with the invention, this objective is achieved by virtue of the fact that the operating program is at least partially stored in a variable memory of the apparatus and during the performance of the update is at least partially replaced by the new operating program.

In accordance with one embodiment of the invention, the device for a medical apparatus consists of an internal or external input device for data inputs and/or computer program inputs or for data reception and/or computer program reception and of a memory device that is at least indirectly connected with said input device, with data or computing and/or counting algorithms stored in one or more memories in the memory device and with testing means that automatically compare the input or received data and/or computer programs, referred to here as "updates", with data stored in one or more memories of the memory device, including especially after or while the update and/or the data stored in one or more memories were or are being processed and especially were or are passing through computing and/or counting algorithms, where control devices are present, which, on the basis of the comparison result determined by the testing means and only in the case of certain well-defined updates, automatically cause the apparatus permanently or temporarily to apply these data, programs, or data or programs computed from them to hardware functions that are associated with these updates and cause the performance of these hardware functions associated with the updates to be disabled by these control devices or by other means without the proper update.

In the context of the invention, operating programs are, for example, the operating software for the operation of the apparatus, application programs, evaluation programs for measured values, or a communication program.

In accordance with another embodiment of the invention, the device for a medical apparatus consists of an internal or external input device for data inputs or data reception and of a memory device that is at least indirectly connected with said input device, with data or computing and/or counting algorithms stored in one or more memories in the memory device and with testing means that automatically compare the input or received data, here: "code", with data stored in one or more memories of the memory device, including especially after or while the code and/or the data stored in one or more memories were or are being processed, where control devices are present, which, on the basis of the comparison result determined by the testing means and only in the case of a certain well-defined code or certain well-defined codes, automatically cause the apparatus to cooperate permanently or temporarily with one or more specific additional internal or external hardware components that are associated with these codes and cause the cooperation of the apparatus with a hardware component associated with the codes to be disabled by these control devices or by other means without the proper code.

Functionality that is optimized for the user is achieved by notifying the user of a positive comparison result by an acoustic, optical or other type of display or signal, e.g., as a success message or signal.

Functionality that is optimized for the user is also achieved by notifying the user of a negative comparison result by an acoustic, optical or other type of display or signal, e.g., as an error message or fault signal.

Expanded functionality is realized by storing in the memory device and/or in the code data which, even in processed or computed form, temporarily limit the execution of the functions and/or the disabling of the functions in a well-defined way.

An individually adaptable application is realized if the apparatus contains hardware components that cannot work without the input of the code and in this respect are disabled for all functions.

An embodiment of the invention with a simple design is realized if the apparatus or parts of it are prevented from being supplied with electric power (e.g., by mains connection, batteries, or secondary cells) without the code input, or the supply is limited in a well-defined way with respect to time or power.

Fast realization of the release is achieved if the code is input or transmitted to the input device by means of a data carrier with patient-related, practice-related, or physician-related data, such as the health card, or by a reading device designed for this purpose.

Effective disabling is realized by disabling certain components of the apparatus, especially sensors that detect certain characteristic data, so that they are at least temporarily disabled for use by the apparatus without the input of the code.

Expanded functionality is produced by storing in the memory device and/or in the code data which, even in processed or computed form, temporarily limit the execution of the hardware functions and/or the disabling of the hardware functions in a well-defined way.

An embodiment of the invention with a simple design is realized if the apparatus contains hardware components that cannot work without the update of the code and in this respect are disabled for all functions.

In accordance with the invention, certain components of the apparatus, especially sensors that detect certain characteristic data, such as wavelengths, are at least temporarily disabled for use by the apparatus without the update.

In accordance with the invention, data which temporarily limit the cooperation of the apparatus with the associated additional hardware component and/or its disabling are stored in the memory device and/or in the code.

In accordance with the invention, alternatively and/or additionally, the apparatus already contains hardware or software components that cannot work without the cooperation of the apparatus with the associated additional hardware component and in this respect are already disabled for all functions.

An embodiment of the invention with respect to the apparatus is realized if the hardware components that are already present and are disabled without the code and/or the additional hardware components are well-defined sensors, especially of a specific wavelength.

In a variant with a simple design, the code is stored in the additional hardware component and/or in the means which connect the additional hardware component with the apparatus and reaches the input device by the creation of the connection between this hardware component and the apparatus.

Increased functionality is produced if an optical or acoustic or mechanical display/signal output is present that keeps display/output possibilities ready for release by code, the upgrade or the additional hardware component, which display/output possibilities cannot be used without their release by code, the upgrade, or the additional hardware component.

Protection from improper use is realized if a well-defined repeated input of one or more false codes or one or more improper updates leads to temporarily limited or unlimited disabling of the acceptance of any additional input for codes or updates, which possibly can be reenabled only with another code (which, for example, is known only by the manufacturer).

In accordance with one embodiment, the invention can be realized as a method for updating software and/or firmware in electronic medical apparatus, where the medical apparatus has a rewritable memory unit for storing an updated and/or a previous version of the software and/or firmware, said method comprising the following steps:

(a) preparation of the software and/or firmware for updating by means of an updating device;

(b) communication of the medical apparatus with the updating device;

(c) when communication has been established: transmission of the update from the updating device to the medical apparatus;

(d) writing the update into a rewritable memory unit;

(e) verification of the update as a valid version and identification of the previous version as invalid; and (f) execution of the updated software and/or firmware.

In accordance with the invention, it is contemplated that the previous version is overwritten with the updated software and/or firmware or is moved to a restore memory, especially if the updated form is released only for a limited time.

In accordance with the invention, it is also contemplated that the medical apparatus additionally contains a permanent memory, including instructions that are executed after the update, whereupon the rewritable memory unit is searched for updated software and/or firmware, which is then loaded and executed.

In accordance with another embodiment, the invention can be realized as a method for updating software and/or firmware in electronic medical apparatus, where the medical apparatus has a microcontroller with a memory unit, and the microcontroller can be driven as follows via a data link, for example, via free PIN's:

(a) transmission of a signal to the microcontroller to effect a reset of the microcontroller, for example, via free PIN's;

(b) preparation of a flash program with new firmware for writing the new firmware onto the microcontroller, (c) where the program entry point is written in a well-defined location of the microcontroller, which is read out for the first time after completion of the reset.

Specific embodiments of the invention are schematically illustrated in the drawings.

FIG. 1 shows a perspective view of a ventilator with a connecting hose running to a ventilation mask.

FIG. 1 shows the basic design of a ventilation device. The housing 1 of the apparatus has an operating panel 2 and a display 3, and a respiratory gas pump is installed inside the apparatus housing 1. A connecting hose 5 is attached by a coupling 4. An additional pressure-measuring hose 6, which can be connected with the apparatus housing 1 by a pressure input connection 7, can run along the connecting hose 5. To allow data transmission, the apparatus housing 1 has an interface 8. Other pieces of medical apparatus can be connected via this interface 8. For example, a pulse oximeter or a pulse spectrometer can be connected. A humidifier can also be adapted.

An expiratory element 9 is installed in an expanded area of the connecting hose 5 that faces away from the apparatus housing 1. An expiratory valve can also be used.

FIG. 1 also shows a patient interface in the form of a ventilator mask 10, which is designed as a nasal mask. The mask can be fastened on the patient's head by a headgear 11. The expanded area of the patient interface 10 that faces the connecting hose 5 has a coupling device 12.

Data can be input and/or output via the interface 8, for example, the dead space volume or a software update or firmware update can be input. The interfaces can be realized in cable-connected form, as infrared interfaces, Bluetooth interfaces, or USB. An oxygen supply valve can be adapted to the ventilator in the area of the apparatus housing. It is also possible to provide additional oxygen enrichment of the respiratory gas in order to improve the oxygen supply to the patient.

In addition, the apparatus can be provided with interfaces for adaptable accessory devices and information management systems, for example, for accepting storage media or for connecting to an EKG, EEG, printer, defibrillator, pulse oximeter, or other medical apparatus.

It is also possible to use a modem or other interface to transmit recorded data to the physician, such as trends, unusual events, warning messages, etc., and to transmit other types of recorded data to the user or to maintenance/customer service personnel, such as peculiarities, operating hours, or other types of information that are useful for ensuring perfect operation.

It is also possible to use an interface to adapt sensors for determining other bodily parameters. For example, adaptable accessory devices, such as an EKG, EEG, EOG, pulse oximeter, and pulse spectrometer, can be added on. The bodily parameters determined by the adapted sensors can be displayed on the ventilator display. Certain areas of the display are reserved for this purpose and are activated only when the given sensor has been adapted. Measured values determined by the given adapted sensors are then displayed in these display areas.

In another embodiment, the device of the invention is realized for a pulse oximeter, which determines oxygen saturation SpO2 by means of at least two wavelengths. In addition, the pulse oximeter has an additional wavelength that can be used for the determination of other parameters, such as methemoglobin or carboxyhemoglobin. This additional function is not released for use in the current configuration of the pulse oximeter, but rather a code must be input to release this function and/or an expanded computing and/or counting algorithm must be installed. The device consists of an input device for data input/data reception, especially for receiving updates or upgrades of the computing and/or counting algorithms of the pulse oximeter, and of a memory device connected with the input device, with computing and/or counting algorithms stored in at least one memory, which algorithms serve the purpose of determining at least the following test parameters: SpO2 and pulse rate.

A code that serves to release the apparatus functions can be input through the input device for data input/data reception, which is realized, for example, as a keyboard.

Testing means compare the input code with a comparison code stored in a memory of the memory device for the purpose of verifying the code, where control devices, on the basis of the comparison result determined by the testing means and only in the case of a certain well-defined code or certain well-defined codes, automatically cause the pulse oximeter at least temporarily to be able to perform certain functions, namely, the determination of the expanded test quantities (e.g., methemoglobin or carboxyhemoglobin) with the use of at least three wavelengths associated with these codes. The execution of these functions associated with the codes is disabled by the control devices or by other means without the proper code.

After the code has been input, the user is notified of a positive comparison result by receiving an acoustic or optical success message, for example, in the form of an LED that shines green.

The user is notified of a negative comparison result by receiving an acoustic or optical error message, for example, in the form of an LED that shines red.

In accordance with the invention, the sensor of the pulse oximeter is already equipped for the determination of additional test parameters, such as methemoglobin and/or carboxyhemoglobin and/or hemoglobin concentration, for example, by virtue of its ability to emit at least three different wavelengths. Two of these wavelengths are used for the determination of SpO2. A code is input to activate at least one additional wavelength, for example, by operating the respective LED of, say, the power supply and evaluating the data of at least three different wavelengths according to a computing and/or counting algorithm to determine the SpO2 and the other test parameters, such as methemoglobin and/or carboxyhemoglobin and/or hemoglobin concentration.

In a preferred embodiment, the supplying of additional LED's with electric power is prevented without the code input.

In another embodiment, the device of the invention is realized for a pulse oximeter that has at least three wavelengths in the range of 500 nm to 950 nm, which are used to determine the parameters of methemoglobin or carboxyhemoglobin and SpO2 and pulse rate. In addition, the sensor of the pulse oximeter has at least one additional wavelength in the range of 950 to 2,500 nm, which can be used to determine the hemoglobin concentration cHb, where this function is not released in the current configuration of the pulse oximeter.

To release the additional wavelength in the range of 950 to 2,500 nm, which is used for determining the hemoglobin concentration, a code must be input. The code releases the corresponding LED and/or an expanded computing and/or counting algorithm, specifically, to allow the determination of the cHb from at least four wavelengths in the range of 500 to 2,500 nm.

In another embodiment, the device of the invention is realized for a pulse oximeter that has at least three wavelengths in the range of 500 nm to 950 nm, which are used to determine the parameters of methemoglobin or carboxyhemoglobin and SpO2 and pulse rate. In addition, the sensor of the pulse oximeter has at least one additional wavelength in the range of 950 to 2,500 nm, which can be used to determine the hemoglobin concentration cHb. To determine, for example, the hemoglobin concentration, an expanded computing and/or counting algorithm is installed via the input device for data input/data reception and stored in a memory in the memory device connected with the input device, where the program entry point of the expanded computing and/or counting algorithm is written in a well-defined memory location, which is read out for the first time.

The computing and/or counting algorithm that was previously used to determine the parameters methemoglobin or carboxyhemoglobin and SpO2 and pulse rate is preferably overwritten or deactivated.

In a supplementary embodiment, the device of the invention for a pulse oximeter consists of an input device for an update and of a memory device that is connected with the input device, with a computing and/or counting algorithm stored in a memory in the memory device, said algorithm serving to determine the parameters SpO2 and methemoglobin and/or carboxyhemoglobin with the use of the data of at least three wavelengths in the range of 500 to 950 nm, where testing means automatically compare the update with data stored in the memories of the memory device, and a control device, on the basis of the comparison result determined by the testing means and only in the case of verification of the update, causes the pulse oximeter to execute the update, where the update serves to determine the parameter hemoglobin concentration with the use of the data of at least four wavelengths in the range of 500 to 2,500 nm.

Alternatively, the device can be realized for a pulse oximeter that is used for determining the parameters SpO2 and pulse rate. To this end, the pulse oximeter uses a sensor with two active LED's that are used for determining SpO2. In addition, the sensor has at least one LED that is not active but can be activated and that serves the purpose of determining at least one additional parameter (selected from the following group: methemoglobin, carboxyhemoglobin, hemoglobin concentration, bilirubin, glucose).

The pulse oximeter has a computing and/or counting algorithm that is used to determine SpO2 and pulse rate. In addition, it can determine at least one other parameter (selected from the following group: methemoglobin, carboxyhemoglobin, hemoglobin concentration, bilirubin, glucose). The pulse oximeter also has an input device for data input and testing means connected with said input device 4.

To activate the unused LED and/or the computing and/or counting algorithm for the additional determination of at least one other parameter (selected from the following group: methemoglobin, carboxyhemoglobin, hemoglobin concentration, bilirubin, glucose), a code is input via the input device for data input and compared by the testing means with the data stored in a memory of the memory device. On the basis of the comparison result determined by the testing means, a control device causes the activation of the unused LED and/or the computing and/or counting algorithm for the additional determination of at least one other parameter (selected from the following group: methemoglobin, carboxyhemoglobin, hemoglobin concentration, bilirubin, glucose), if the input code has been verified by the testing means.

In another embodiment, the pulse oximeter has a display that keeps display/output possibilities ready for release only after release by a code or after an upgrade has been carried out. Thus, during the operation of the apparatus, before the update is performed, for example, the parameters SpO2 and pulse rate are displayed. After the update has been performed, the display/output is activated in the display area to display the parameters methemoglobin and/or carboxyhemoglobin and/or hemoglobin concentration and/or bilirubin and/or glucose, for example in the form: SaMet, SaCO, SaO2, cHb, where cHb and glucose are displayed in g/dL, and, for example, SaMet and SaCO are displayed in %. These are only some of the possible applications, which can also apply to other parameters.

For example, the display range for the concentration of hemoglobin cHb is 5 to 25 g/dL. Alternatively or additionally, a display in mmol/L may be provided. The display range for a carbon monoxide fraction in the blood is 0% to 60%.

In accordance with the invention, it is also possible to perform an update for the determination of the parameter bilirubin. In accordance with the invention, the update is carried out starting from at least two different wavelengths selected from the group comprising 300 nm±15%, 400 nm±15%, 460 nm±15%, 480 nm±15%, 520 nm±15%, 550 nm±15%, 560 nm±15%, 606 nm±15%, 617 nm±15%, 620 nm±15%, 630 nm±15%, 650 nm±15%, 660 nm±15%, 705 nm±15%, 710 nm±15%, 720 nm±15%, 805 nm±15%, 810 nm±15%, 880 nm±15%, 905 nm±15%, 910 nm±15%, 950 nm±15%, 980 nm±15%, 980 nm±15%, 1,050 nm±15%, 1,200 nm±15%, 1,310 nm±15%, 1,380 nm±15%, 1,450 nm±15%, 1,600 nm±15%, 1,800 nm±15%, 2,000 nm±15%, 2,500 nm±15%, and expanding to at least three different wavelengths selected from the group comprising 300 nm±15%, 400 nm±15%, 460 nm±15%, 480 nm±15%, 520 nm±15%, 550 nm±15%, 560 nm±15%, 606 nm±15%, 617 nm±15%, 620 nm±15%, 630 nm±15%, 650 nm±15%, 660 nm±15%, 705 nm±15%, 710 nm±15%, 720 nm±15%, 805 nm±15%, 810 nm±15%, 880 nm±15%, 905 nm±15%, 910 nm±15%, 950 nm±15%, 980 nm±15%, 980 nm±15%, 1,050 nm±15%, 1,200 nm±15%, 1,310 nm±15%, 1,380 nm±15%, 1,450 nm±15%, 1,600 nm±15%, 1,800 nm±15%, 2,000 nm±15%, 2,500 nm±15%.

In accordance with the invention, it is also conceivable, starting from at least two wavelengths, to expand to at least four wavelengths via an update, with the four wavelengths being selected from the group comprising 300 nm±15%, 400 nm±15%, 460 nm±15%, 480 nm±15%, 520 nm±15%, 550 nm±15%, 560 nm±15%, 606 nm±15%, 617 nm±15%, 620 nm±15%, 630 nm±15%, 650 nm±15%, 660 nm±15%, 705 nm±15%, 710 nm±15%, 720 nm±15%, 805 nm±15%, 810 nm±15%, 880 nm±15%, 905 nm±15%, 910 nm±15%, 950 nm±15%, 980 nm±15%, 980 nm±15%, 1,050 nm±15%, 1,200 nm±15%, 1,310 nm±15%, 1,380 nm±15%, 1,450 nm±15%, 1,600 nm±15%, 1,800 nm±15%, 2,000 nm±15%, 2,500 nm±15%.

To determine the hemoglobin concentration cHb, the invention provides, for example, that, starting from at least two wavelengths, the number of wavelengths is expanded to at least three via an update, such that there is high absorption for water at least at one wavelength selected from the group comprising 950 nm±15%, 980 nm±15%, 980 nm±15%, 1,050 nm±15%, 1,200 nm±15%, 1,310 nm±15%, 1,380 nm±15%, 1,400 nm±15%, 1,450 nm±15%, 1,500 nm±15%, 1,550 nm±15%, 1,600 nm±15%, 1,700 nm±15%, 1,800 nm±15%, 1,900 nm±15%, 2,000 nm±15%, 2,500 nm±15%.

In accordance with the invention, it is also possible to connect an apparatus that is used for medicinal, medical, or health-related purposes, especially a measuring apparatus, diagnostic apparatus or therapeutic apparatus, at least temporarily with an adaptable accessory device, for example, an EKG, EEG, EOG, printer, monitor, defibrillator, pulse oximeter or other medical apparatus. In this case, it is also provided that the adaptable accessory device be released by a code input.

The invention claimed is:

1. A method for updating software or firmware in an electronic ventilation device that comprises (i) a housing comprising an operating panel, a display, a USB interface, a hose attached to the housing through a coupling, and a respiratory gas pump installed in the housing, and (ii) a microcontroller having a rewritable memory unit for storing an updated or a previous version of the software or firmware, said method comprising:
   (a) providing the software or firmware for updating by an updating device;
   (b) communication of the ventilation device with the updating device via the USB interface;
   (c) when communication has been established, transmission of the update from the updating device to the ventilation device;
   (d) writing the update into a rewritable memory unit;
   (e) verification of the update as a valid version and identification of the previous version as invalid; and
   (f) execution of the updated software or firmware, the previous version of the software or firmware being overwritten with the updated software or firmware or being moved to a restore memory, whereby an operating program stored in the ventilation device is at least partially replaced by a new operating program; the microcontroller being driven via a data link as follows:
1. transmitting a signal to the microcontroller to reset the microcontroller;
2. providing a flash program with new firmware for writing the new firmware into the microcontroller; and
3. writing a program entry point in a well-defined location of the microcontroller, which is read-out first after completion of the reset.

2. The method of claim 1, wherein the previous version of the software of firmware is overwritten with the updated version of the software or firmware.

3. The method of claim 1, wherein the previous version of the software or firmware is moved to a restore memory.

4. The method of claim 1, wherein after the update, instructions present in a permanent memory are executed, whereupon a rewritable memory unit is searched for updated software or firmware, which is then loaded and executed.

5. The method of claim 1, wherein a base operating program that cannot be altered by the updating is stored in the ventilation device.

6. The method of claim 1, wherein a testing element of the ventilation device compares an input code with a reference value.

7. The method of claim 6, wherein at least one function of the device is released only when the input code agrees with the reference value.

8. The method of claim 6, wherein a user is notified of a positive comparison result by an acoustic or optical display or message.

9. The method of claim 6, wherein a user is notified of a negative comparison result by an acoustic or optical display or message.

10. The method of claim 1, wherein a hardware component present in the ventilation device is activated by the updated software or firmware.

11. The method of claim 1, wherein a functionality of a hardware component present in the ventilation device is altered by the updated software or firmware.

12. The method of claim 1, wherein data are stored in a memory device or in a code of the ventilation device, which data temporarily limit execution of functions or disabling of functions in a defined way.

13. The method of claim 1, wherein the ventilation device comprises at least one hardware component that cannot work without input of a code and in this respect is disabled for all functions at least temporarily.

14. The method of claim 13, wherein the at least one hardware component comprises a sensor comprising characteristic data.

15. The method of claim 13, wherein the characteristic data comprise a wavelength of the sensor.

16. The method of claim 1, wherein the ventilation device or parts of it are prevented from being supplied with electric power without code input, or supply is limited in a defined way with respect to time or power.

* * * * *